(12) United States Patent
Deschner et al.

(10) Patent No.: US 12,104,824 B2
(45) Date of Patent: Oct. 1, 2024

(54) LOW-PROFILE IN-DUCT AIR SANITIZER USING UV EMITTER AND COOPERATING WALL-MOUNTABLE REFLECTORS

(71) Applicant: AIR Alpine Innovative Research Inc., Calgary (CA)

(72) Inventors: Bernard Deschner, Calgary (CA); Stuart Henley, Calgary (CA)

(73) Assignee: AIR Alpine Innovative Research Inc., Calgary (CA)

( * ) Notice: Subject to any disclaimer, the term of this patent is extended or adjusted under 35 U.S.C. 154(b) by 196 days.

(21) Appl. No.: 17/513,107

(22) Filed: Oct. 28, 2021

(65) Prior Publication Data
US 2023/0134766 A1   May 4, 2023

(51) Int. Cl.
*F24F 8/22* (2021.01)
*A61L 9/20* (2006.01)

(52) U.S. Cl.
CPC .............. *F24F 8/22* (2021.01); *A61L 9/20* (2013.01); *A61L 2209/12* (2013.01); *A61L 2209/15* (2013.01); *A61L 2209/16* (2013.01)

(58) Field of Classification Search
None
See application file for complete search history.

(56) References Cited

U.S. PATENT DOCUMENTS

| | | | | |
|---|---|---|---|---|
| 2004/0084639 A1* | 5/2004 | Guzorek | ................ | F24F 8/22 |
| | | | | 250/504 R |
| 2012/0023992 A1* | 2/2012 | Sevack | ................ | A61L 9/20 |
| | | | | 62/264 |
| 2012/0168641 A1* | 7/2012 | Lizotte | ................ | C02F 1/325 |
| | | | | 250/503.1 |

FOREIGN PATENT DOCUMENTS

| | | | | |
|---|---|---|---|---|
| GB | 2427113 A | * 12/2006 | ............... | A61L 2/10 |
| WO | WO-2006131720 A1 | * 12/2006 | ............... | A61L 2/10 |

* cited by examiner

*Primary Examiner* — Andrew Smyth
(74) *Attorney, Agent, or Firm* — Kyle R Satterthwaite; Ryan W Depuis; Ade & Company Inc.

(57) ABSTRACT

An in-duct air sanitization apparatus features an air sanitizer, and a set of reflectors. A housing of the sanitizer is mountable to a first wall of an HVAC duct, and a UV emitter resides on a working side of the housing that faces into the HVAC duct to irradiate the duct interior with UV light. The reflectors are mountable on interior wall surfaces of the duct to receive and reflect incident light from the sanitizer to ensure thorough irradiation of an entire cross-sectional flow area of the duct interior, thus optimizing the effective UV sterilization of the airflow. The emitter is oriented with one or more bulb axes thereof oriented parallel to the working side of the housing to provide the sanitizer with a compact and conveniently handled low-profile design. The reflectors are mounted magnetically to the duct walls in tool-free fashion with no detriment to duct wall integrity.

21 Claims, 5 Drawing Sheets

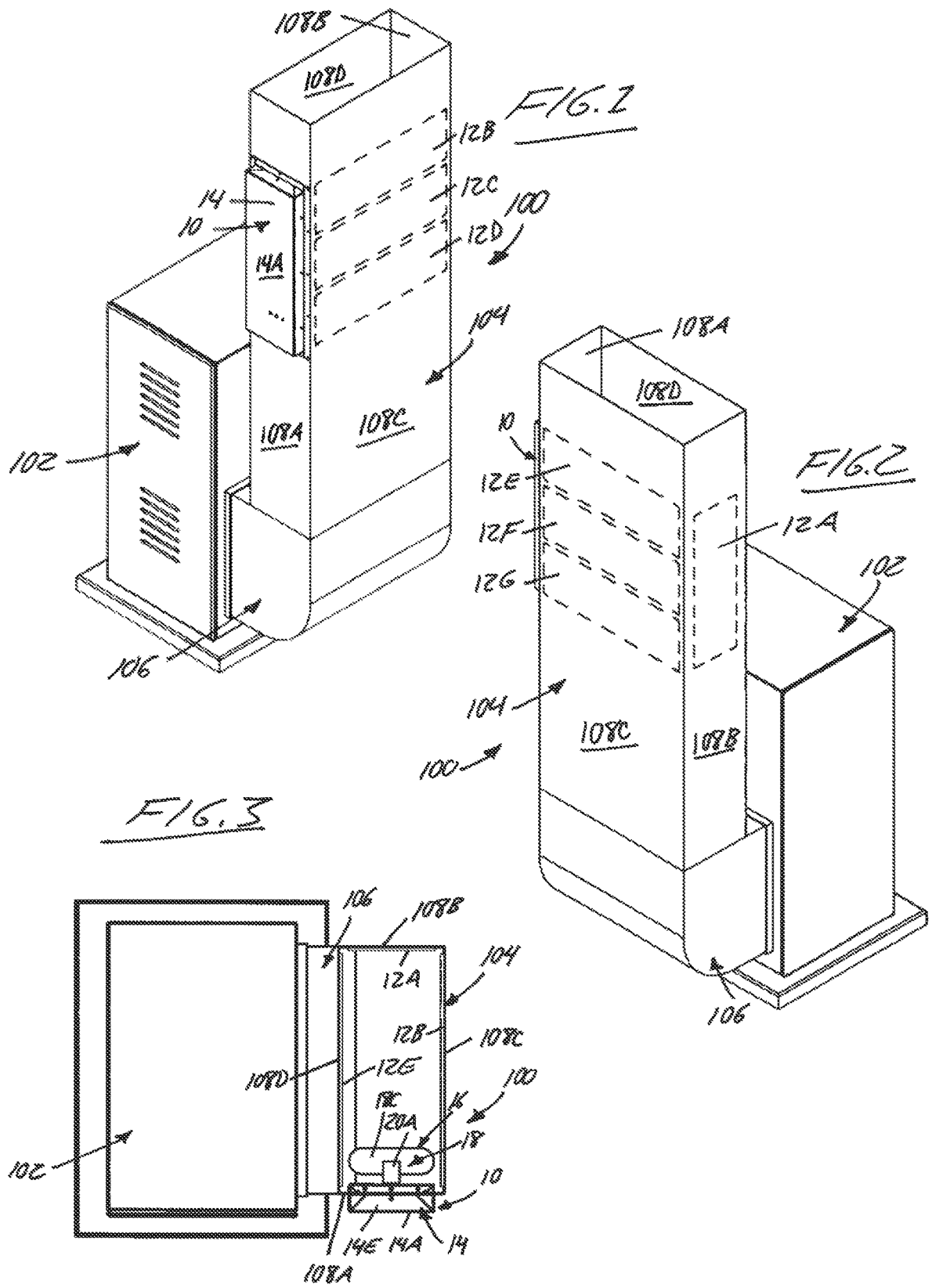

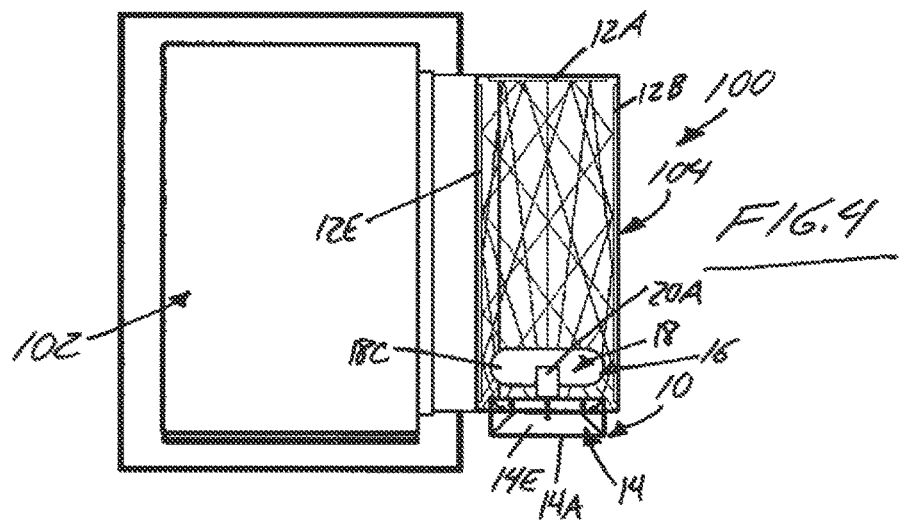
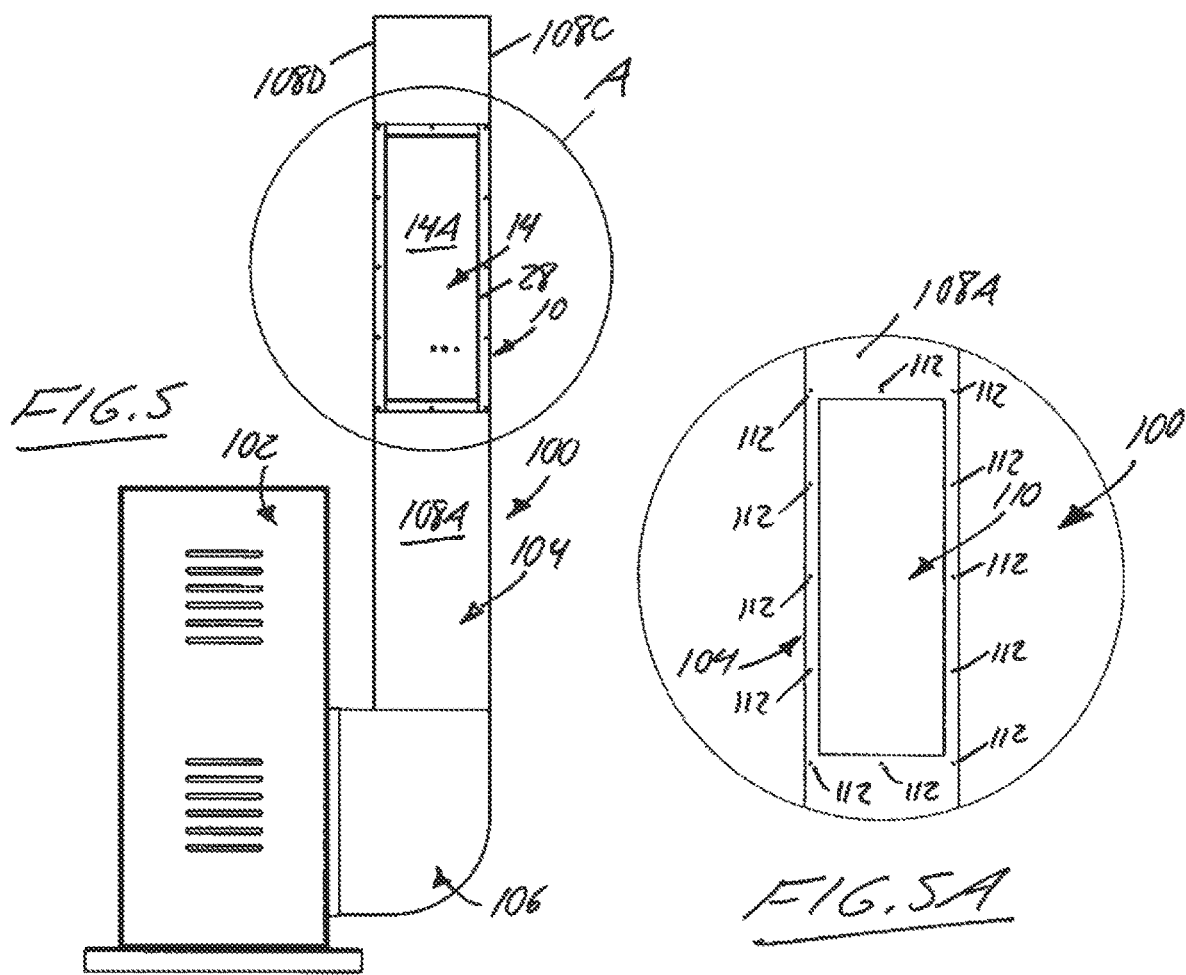

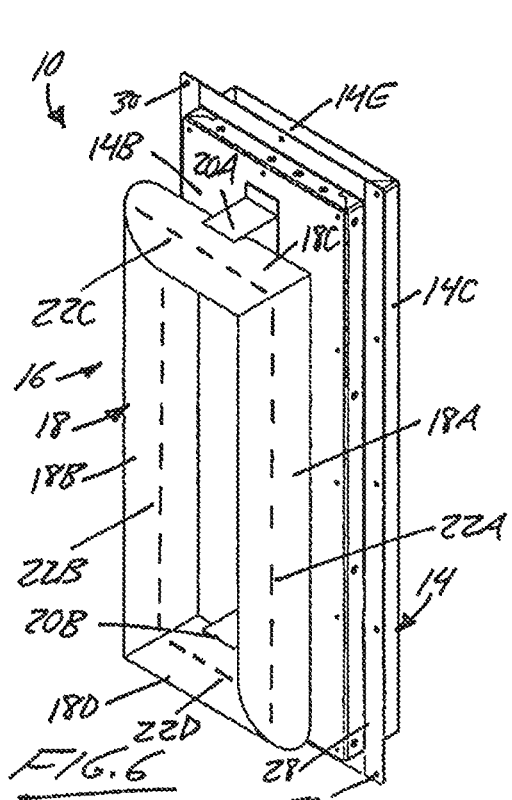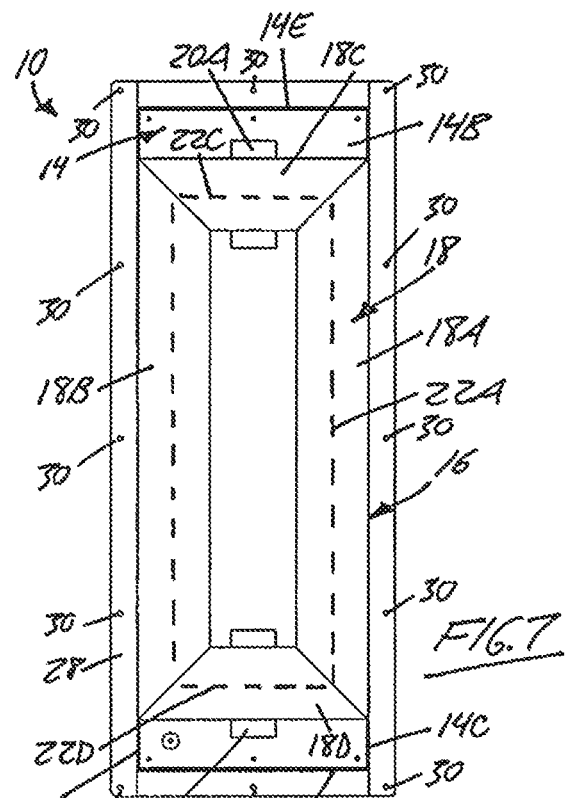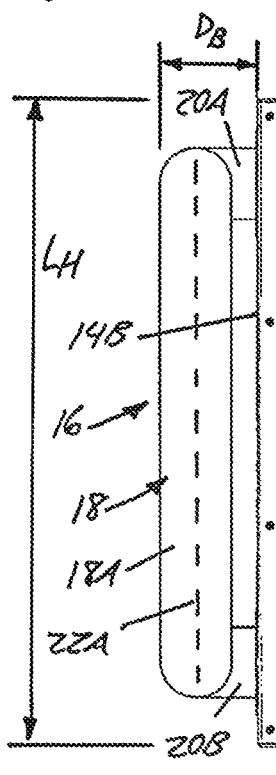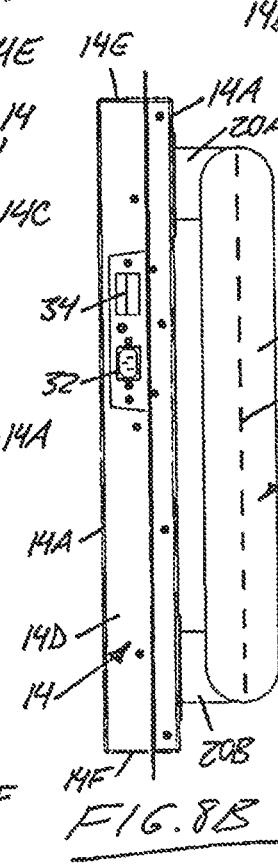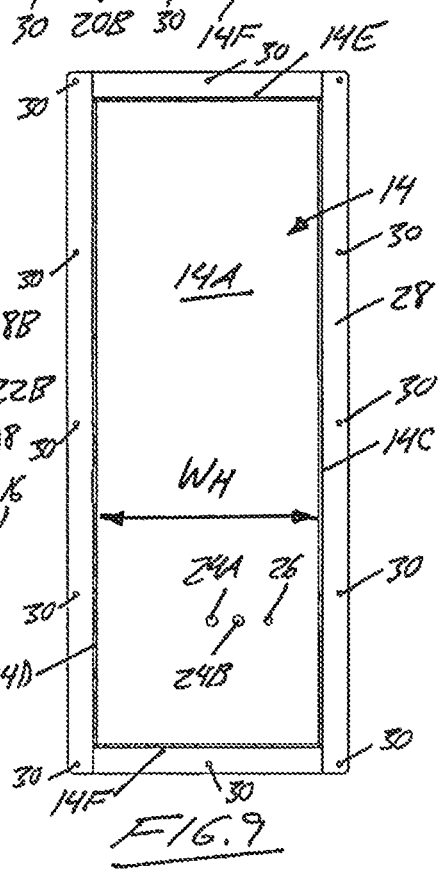

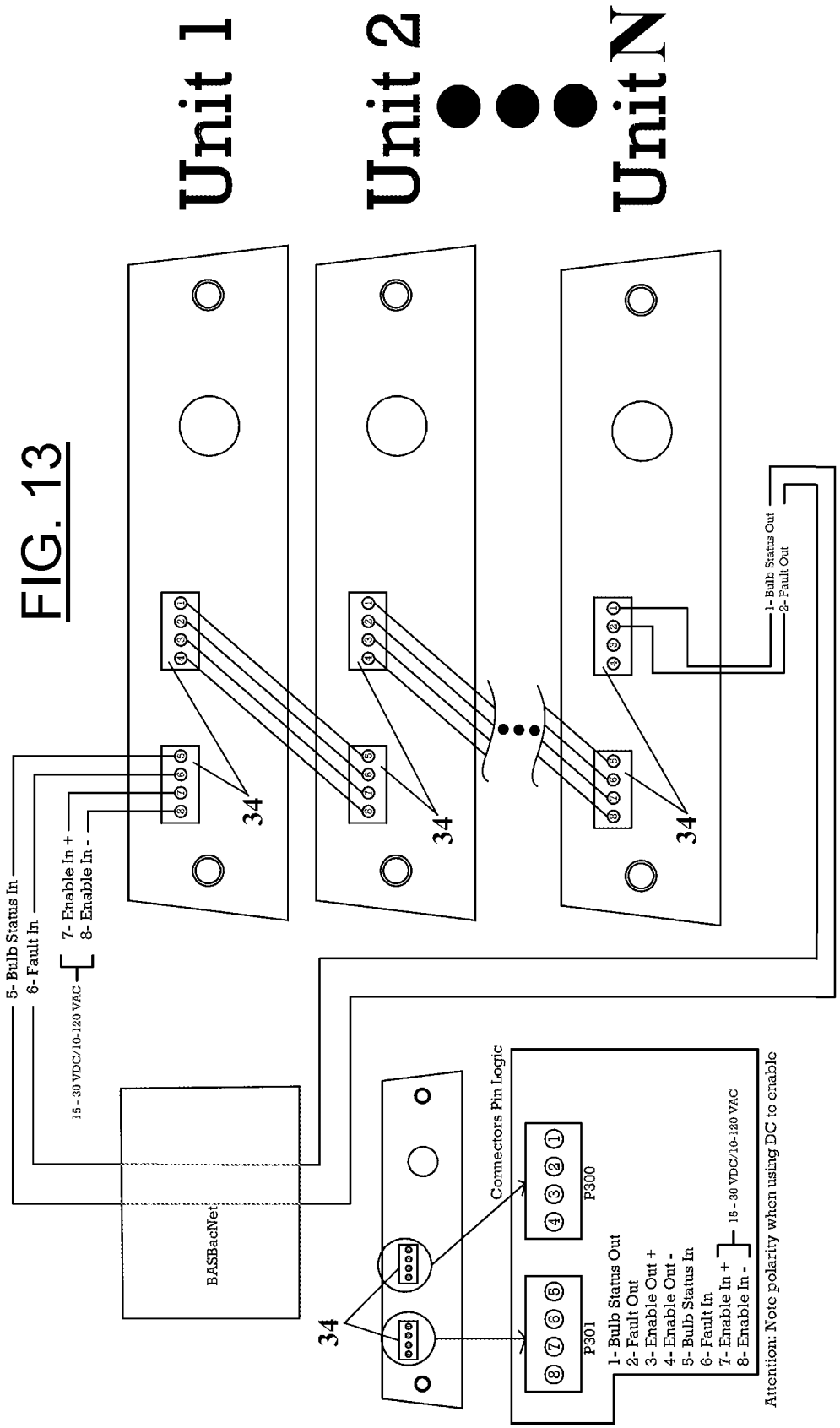

LOW-PROFILE IN-DUCT AIR SANITIZER USING UV EMITTER AND COOPERATING WALL-MOUNTABLE REFLECTORS

FIELD OF THE INVENTION

This application relates generally to UV-based sanitization of airflow in an HVAC system, and more particularly to in-duct UV-based air sanitizers that are mountable to the ductwork of such HVAC systems.

BACKGROUND

While UV-based devices for sanitizing airflow in HVAC systems are found in the prior art, the COVID-19 pandemic has particularly emphasized a greater need than eve for effective solutions in this field. Prior art in this field of endeavour includes UV-based air sanitizers designed for installation in ductwork of an HVAC system, examples of which can be seen in U.S. Pat. Nos. 5,894,130, 5,968,455, 6,797,966, 7,107,778, 7,238,326, 8,753,575, 8,772,744, US20040213703, US20050163652, US20050163668, US20080279733, US20140294666, and US20180361007. In contrast to in-duct equipment installed within sections of the HVAC ductwork, other prior art HVAC air sanitizers included combined filtration and UV sterilization devices, or specially fabricated sterilization chambers that are installed in-line with the HVAC ductwork, thus requiring a more complex installation process, especially when retrofitting into a pre-existing HVAC system. Examples of such designs can be seen in U.S. Pat. Nos. 5,523,057, 7,875,247 and US20120315184. Despite these prior endeavours, there remains room for improvement, and particularly a need for effective solutions that can be easily integrated into an existing HVAC system.

Disclosed herein is Applicant's unique in-duct air sanitization solution with a novel and inventive combination of features not heretofore seen in the prior art.

SUMMARY OF THE INVENTION

According to one aspect of the invention, there is provided an in-duct air sanitization apparatus comprising:
an air sanitizer comprising:
a housing configured for mounting thereof to a wall of an HVAC duct inside of which a forced airflow is to be sanitized; and
a UV emitter mounted on a working side of the housing that faces into the HVAC duct when installed thereon and operable to irradiate an interior of said HVAC duct with UV light; and
one or more reflectors mountable on one or more interior wall surfaces of the HVAC duct to receive and reflect incident light from the UV emitter to create thorough UV coverage throughout a cross-sectional flow area of the duct.

According to another aspect of the invention, there is provided an in-duct air sanitization apparatus comprising:
an air sanitizer comprising:
a housing configured for mounting thereof to a wall of an HVAC duct inside of which a forced airflow is to be sanitized, said housing containing electronic operating components of said air sanitizer; and
a UV emitter supported in said housing in a position residing externally of the housing at a working side thereof that faces into the HVAC duct when installed thereon, said UV emitter being operable by said electronic operating components to irradiate an interior of said HVAC duct with UV light, and said UV emitter comprising one or more UV bulbs each composed of one or more tubular segments having a longitudinal axis along which the tubular segment is elongated, and that lies in an orientation that is more parallel than perpendicular to said working side of housing such that said UV emitter lies more parallel than perpendicular to said wall of the HVAC duct.

According to yet another aspect of the invention, there is provided a method of installing an UV-based air sanitizer in an HVAC duct that has a plurality of duct walls delimiting an interior duct space having a cross-sectional flow area, said method comprising:
(a) to an interior wall surface of at least a subset of said duct walls, mounting one or more reflectors for the purpose of receiving and reflecting incident UV light from the air sanitizer to create thorough UV coverage throughout said cross-sectional flow area of the duct; and
(b) mounting said UV-based air sanitizer to one of said duct walls in an installed position in which a UV emitter of said air sanitizer is operable to irradiate the interior duct space, and the one or more reflectors mounted therein, with UV light, and thereby generate said thorough UV coverage throughout said cross-sectional flow area of the duct.

BRIEF DESCRIPTION OF THE DRAWINGS

One embodiment of the invention will now be described in conjunction with the accompanying drawings in which:

FIG. 1 is a perspective view of an UV-based HVAC air sanitization apparatus of the present invention installed on a return air duct of a residential furnace.

FIG. 2 is another perspective view of the installed apparatus of FIG. 1 from an opposing side of said furnace.

FIG. 3 is an overhead plan view of the installed apparatus of FIG. 1.

FIG. 4 is another overhead plan view of the installed apparatus of FIG. 3, schematically illustrating thorough UV irradiation of an interior of the air duct throughout a full cross-sectional flow area thereof.

FIG. 5 is a side elevational view of the installed apparatus of FIG. 1.

FIG. 5A is a partial closeup view of the return air duct of the furnace of FIG. 5, in isolation, at the area thereof denoted by detail circle A.

FIG. 6 is an isolated perspective view of an air sanitization unit of the apparatus of FIG. 1, from a rear working side thereof that faces into the duct when installed thereon.

FIG. 7 is an elevational rear view of the air sanitization unit of FIG. 6 showing the rear working side thereof.

FIG. 8A is an elevational edge view of the air sanitization unit of FIG. 6.

FIG. 8B is another elevational edge view of the air sanitization unit of FIG. 7 from an opposing viewpoint.

FIG. 9 is an elevational front view of the air sanitization unit of FIG. 6 showing a front display side thereof that faces outwardly from duct when installed thereon.

FIG. 13 schematically illustrates daisy-chained installation of a plurality of the air sanitization units in networked connection to a control panel of a building automation system (BAS).

DETAILED DESCRIPTION

Figure 10:
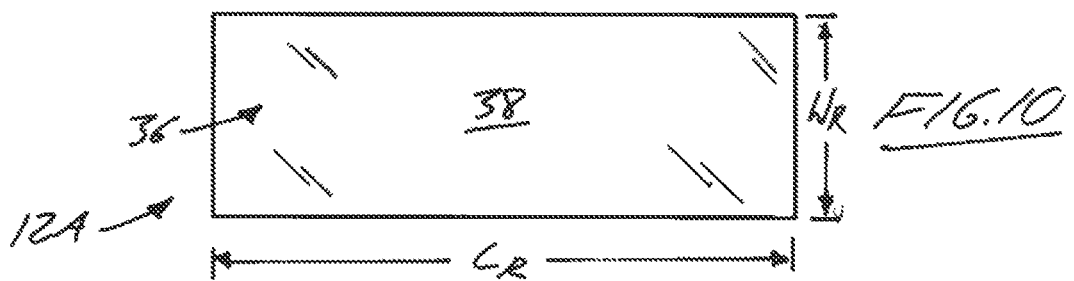
FIG. 10 is an isolated plan view of a reflective working side of a singular wall-mountable reflector of the apparatus of FIG. 1, for installation an interior wall surface of the duct.

With initial reference to FIG. 1, illustrated therein is UV-based HVAC air sanitization apparatus of the present invention, installed in this non-limiting example on return air ductwork 100 of a residential furnace 102. More particularly, the illustrated example is installed on a vertically upright return air duct 104 that feeds into a return air intake of the furnace 102 via an elbow boot 106 at the bottom of the upright return air duct 104. In this example, the air duct 104 is a rectangular duct whose four walls include first and second narrow duct walls 108A, 108B of equal width and opposing positional relationship to one another, and third and fourth wide duct walls 108C, 108D of equal width and opposing positional relationship to one another. The wide duct walls 108C, 108D are wider than the narrow duct walls 108A, 108B and span therebetween in perpendicular relationship thereto.

The installed air sanitization apparatus is composed of an air sanitization unit 10 for installation on one of the duct walls 108A-108D, and an accompanying set of wall-mountable reflectors 12A-12F for installation on interior wall surfaces of the remainder of the duct walls for cooperation with the air sanitization unit 10 to ensure thorough distribution of UV light from the air sanitization unit 10 throughout an entirety of the air duct's internal cross-sectional flow area, thus ensuring thorough and effective UV-based sterilization of the airflow moving therethrough. In the non-limiting example of the illustrated embodiment, the air sanitization unit 10 is mounted on the narrow first duct wall 108A of the air duct 104, and the set of reflectors 12A-12F are installed in distributed fashion among the narrow second duct wall 108B and the wide third and fourth duct walls 108C, 108D.

In the illustrated embodiment, the air sanitization unit 10 is of elongated rectangular shape, whose overall width is no greater than that of the two narrow duct walls 108A, 108B, and whose length is no greater than that of the two wide duct walls 108C, 108D. The reflectors 12A-12F of the illustrated embodiment are all identical to one another, and likewise are of elongated rectangular shape whose overall width is no greater than that of the two narrow duct walls 108A, 108B, and whose length is no greater than that of the two wide duct walls 108C, 108D. Advantageous sizing relationships between the air sanitization unit 10, the reflectors 12A-12F and the walls 108A-108D of the ductwork 100 in preferred embodiments of the invention are described herein further below in more detail, but more detail concerning the preferred design of the air sanitization unit 10 itself is first set forth as follows.

The air sanitization unit 10 is shown in isolation in FIGS. 6 through 9, and features a housing 14 whose shape is that of a rectangular parallelopiped of greater length than width, and greater width than thickness. A facial front wall 14A of the housing 14 is one of the two largest rectangular sides of the housing's parallelopiped shape, of which the other is a matching and opposing facial rear wall 14B of equal size an shape to the facial front wall 14A. A remaining four perimeter walls 14C-14F of the housing 14 serve to interconnect the facial front and rear walls 14A, 14B to one another around the four perimeter boundaries thereof. These perimeter walls 14C-14F include two lengthwise perimeter walls 14C, 14D that span the elongated length dimension of the housing, and two widthwise perimeter walls 14E, 14F that span the lesser width dimension of the housing. The distance between the facial front and rear walls 14A, 14B and spanned by the perimeter walls 14C-14F denotes the even lesser thickness dimension of the housing.

The interior space of the housing 14 delimited between the housing walls 14A-14F contains all of the working electronics of the air sanitization unit. The facial rear wall 14B defines an interior working side of the housing that faces into the interior space of the air duct 104 when the unit 10 is installed on a duct wall 108A thereof.

Mounted to the facial rear wall 14B of the housing 14 is a UV-emission device 16 composed of one of more UV bulbs 18 operable to emit ultraviolet light, and more particularly, UV light in the UV-C wavelength range. In the non-limiting illustrated embodiment, the UV-emission device is composed of a singular UVC bulb having an O-shaped configuration composed of four tubular segments 18A-18D of linear configuration that are connected together end-to-end in a closed loop of O-shaped appearance, when viewed straight on from the rear working side of the unit 10. Of these four bulb segments 18A-18D, two lengthwise bulb segments 18A, 18B lie parallel to one another and run in the lengthwise direction of the housing 14. These lengthwise bulb segments 18A, 18B reside at respective positions closely neighbouring the planes of the housing's lengthwise perimeter walls 14C, 14D of the housing, and are both contained entirely within the space delimited between those planes. The two remaining widthwise bulb segments 18C, 18D lie parallel to one another and run in the widthwise direction of the housing 14 at respective positions closely neighbouring the planes of the widthwise perimeter walls 14E, 14F of the housing, and contained entirely within the space delimited between those planes.

The lengthwise bulb segments 18A, 18B are longer than the widthwise bulb segments 18C, 18D, and span a substantial majority or near entirety of the length dimension of the facial rear wall 14B of the housing 14. Respective linear axes 22A-22D of the four bulb segments 18A-18D are coplanar with one another in a plane residing parallel to the plane housing's facial rear wall 14B. The bulb is held in slightly offset relation from the plane of the housing's facial rear wall 14B by standoffs, for example a pair of such standoffs 20A, 20B that support the widthwise bulb segments 18C, 18D at opposite ends of the bulb 18, and through which connection of the bulb to the lamp ballast, which is located within the housing 14 along with the other working electronics inside the housing 14. In the illustrated example, the widthwise bulb segments 18C, 18D are offset more inwardly from the respective perimeter boundaries of the of the housing than their lengthwise counterparts 18A, 18B to accommodate adequate room for attachment of the standoffs 20A, 20B to the facial rear wall 14B of the housing 14. Accordingly, the O-shaped configuration of the bulb doesn't quite span the full housing length.

The longitudinal axis 22A-22D of each tubular bulb segment 18A-18D of the UV emitter 16 lies parallel to the inner working side of the housing 14, which in turn lies parallel to the respective duct wall 108A on which the housing 14 is mounted in the installed state of the unit 10, whereby each tubular segment 18A-18D of the UV emitter 16 of the installed unit 10 has its longitudinal axis 22A-22D oriented parallel to the plane respective duct wall 108 on which the unit 10 is installed. The result is a low-profile air sanitization unit 10 of minimal invasiveness into the interior airflow space of the ductwork 100, compared to prior art designs in which the longitudinal axes of tubular UV bulbs instead reside perpendicular to the plane of the duct wall on which they are mounted, and project across an entirety or near entirety of the duct's internal cross-section. This novel low-profile design of the unit 10 makes for easier handling thereof during the installation process.

The facial front wall 14A of the housing 14 defines an outer display side of the unit 10 that faces outwardly from the air duct 104 in the unit's installed position thereon. At this display side of the housing 14, the unit 10 includes one or more visual indicators 24A-24B of the unit's operating status, for example preferably including both a power status indicator 24A, and one or more lamp status indicators 24B. The lamp status indicator(s) illuminate(s) in visually distinct states (e.g. different colours, and/or different continuous vs. blinking patterns, etc.) to reflect different statuses of the UV emitter 16. The illustrated example employs a singular lamp status indicator 24B that illuminates in different colours to reflect different possible operational states: for example illuminating in a first "lamp okay" state (e.g. in solid green) when the working electronics have determined that the UV emitter 16 is operating properly, illuminating in a second "lamp warning" state (e.g. in sold yellow) when the working electronics have determined that the bulb 18 of the UV emitter 16 is nearing an anticipated end of its expected useful operating life, and illuminating in a third "lamp expired" state (e.g. in solid red) when the working electronics identify that the bulb 18 has exceeded the anticipated end of its expected useful operating life.

In addition to detection of these different operating states, the working electronics are also operable to detect a "lamp failure" state of the UV emitter 16, for example based on measured ballast current, in which case the lamp status indicator 24B may illuminate in yet another visually distinct fashion (e.g. in flashing red). An audible alarm may be included for activation in the event of detected lamp failure, and optionally also in the event of the detected "lamp expired" state, in which case, two audibly distinct alarm sounds may optionally be employed for these different detected events. In embodiments that include the lamp life monitoring and indicating functions described above, a lamp life reset button 26 is also provided for manual depression thereof by service personnel when the bulb 18 is replaced so as to reinitiate countdown of a new expected lamp life period.

For mounting of the housing 14 to the duct wall 108A, a mounting flange 28 spans around the full perimeter of the housing 14 in outwardly projecting relationship from the four perimeter walls 14C-14F thereof at a plane residing intermediately between, and parallel to, the front and rear facial walls 14A, 14B of the housing 14. The mounting flange 28 has fastening apertures 30 therein at spaced intervals around the perimeter of the housing 14 to enable fastening of the mounting flange 28 to the exterior of the duct wall 108A using suitable fasteners, for example self-drilling screw fasteners.

Referring to FIG. 8B, a power connection port 32 is provided for connection of a power cord (not shown) by which the unit 10 is connectable to an AC mains power outlet for powering of the lamp ballast and other working electronics of the unit 10. The illustrated embodiment also includes a wiring terminal 34 by which the unit 10 can be communicably connected to a control panel 200 of a building automation system (BAS), and to one more additional air sanitation units of the same or similar design installed in the same building. In one non-limiting example, schematically illustrated in FIG. 13, an eight-pin wiring configuration is used, in which a four-pin output group of terminal pins includes a bulb status output pin (1), a fault output pin (2), and positive and negative enablement output pins (3 & 4), while a corresponding four-pin input group of terminal pins includes a bulb status input pin (5), a fault input pin (6), and positive and negative enablement input pins (7 & 8). In the event of a detected "lamp failure" or "lamp expiration" state by a local on-board controller included among the working electronics of each unit 10, the local controller changes an on/off state at the status output pin (5) from its default state to the opposite state, thus creating a detectable alarm signal sent onward to the connected BAS control panel 200, via other daisy-chained air sanitization units if so installed.

Referring again to FIG. 8B, the illustrated embodiment has both the power connection port 32 and the wiring terminal 34 on the same perimeter wall 14D of the housing, specifically on an outer fraction thereof that resides between the planes of the mounting flange 28 and the facial front wall 14A, so that the power connection port 32 and the wiring terminal 34 both reside outside the air duct 106 in the unit's installed position. It will be appreciated however that either or both of these components may be relocated elsewhere on the housing. Likewise, though placement of the indicators 24A, 24B and lamp life reset button 26 on the facial front wall 14A is optimal for the most convenient visual detection and access, they may be positioned elsewhere on the housing.

The enablement input pins (7 & 8) allow a singular unit 10 to be remotely switched between active/inactive states by the BAS, and in combination with enablement output pins (3 & 4), also allow a bank of daisy chained units 10 to be likewise switched between active/inactive states. To maximize lamp life, each unit 10 preferably includes a pressure switch that is installed at the working side of the unit 10 so as to reside inside the air duct, and is connected to the local onboard controller so that the UV emitter 16 is only activated in the presence of detected airflow inside the air duct. In daisy chained scenarios, the lamp activation/deactivation routine executed by the controller uses not only detected air pressure, but also detected presence/absence of an activation signal on the enablement input pins (7 & 8) as a further input condition on the decision of whether to activate the UV emitter when airflow is detected. So, for example, the BAS can be used to activate a larger quantity of directly wired units 10, or larger quantity of daisy chained banks of units 10, during higher airflow periods, and a activate a lesser quantity of units/banks during lower airflow periods (e.g. higher airflow during daytime business hours, vs. lower airflow during overnight/weekend HVAC down-turn).

Figure 11:
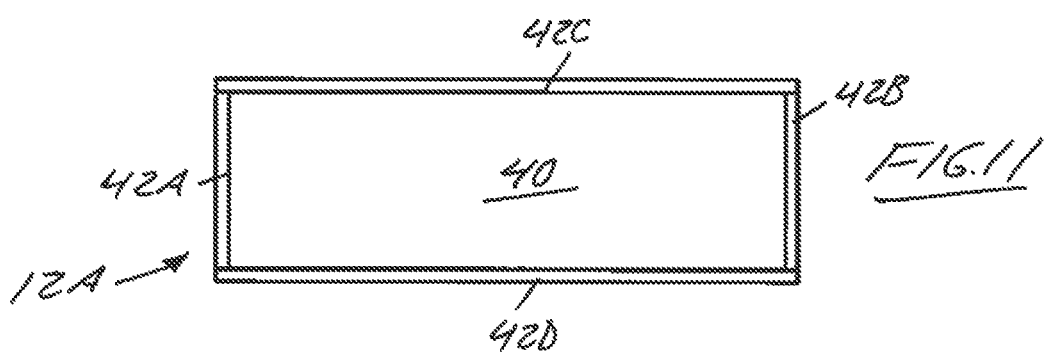
FIG. 11 is a plan view of an opposing magnetic mounting side of the wall-mountable reflector of FIG. 10.

FIGS. 10 and 11 illustrate a singular one of the reflectors 12A-12F, of which the other reflectors are identical in the illustrated embodiment. The reflector 12A is of flat rectangular shape, and on a frontside 36 thereof, features a reflective surface 38, preferably spanning the full rectangular area the reflector's frontside 36. The opposing backside 40 is referred to as a mounting side of the reflector, which is to be attached to an interior wall surface of one of the duct walls 108A-108D during installation. The preferred embodiment employs fastener-free magnetic mounting of the reflectors 12A-12D to the metal walls of the air duct 106 via one or more magnets on each reflector. The illustrated reflector 12A of FIG. 11 thus features multiple magnets on the backside 40 thereof, for example embodied by four pieces of magnetic tape 42A-42D each spanning a respective outer margin of the reflector's backside 40 along a respective perimeter edge thereof. As shown, each such length of magnetic tape 42A-42D may span an entirety of the respective perimeter edge of the reflector, whereby the four pieces 42A-42D collectively span the full perimeter of the reflector's backside 40.

Figure 12:
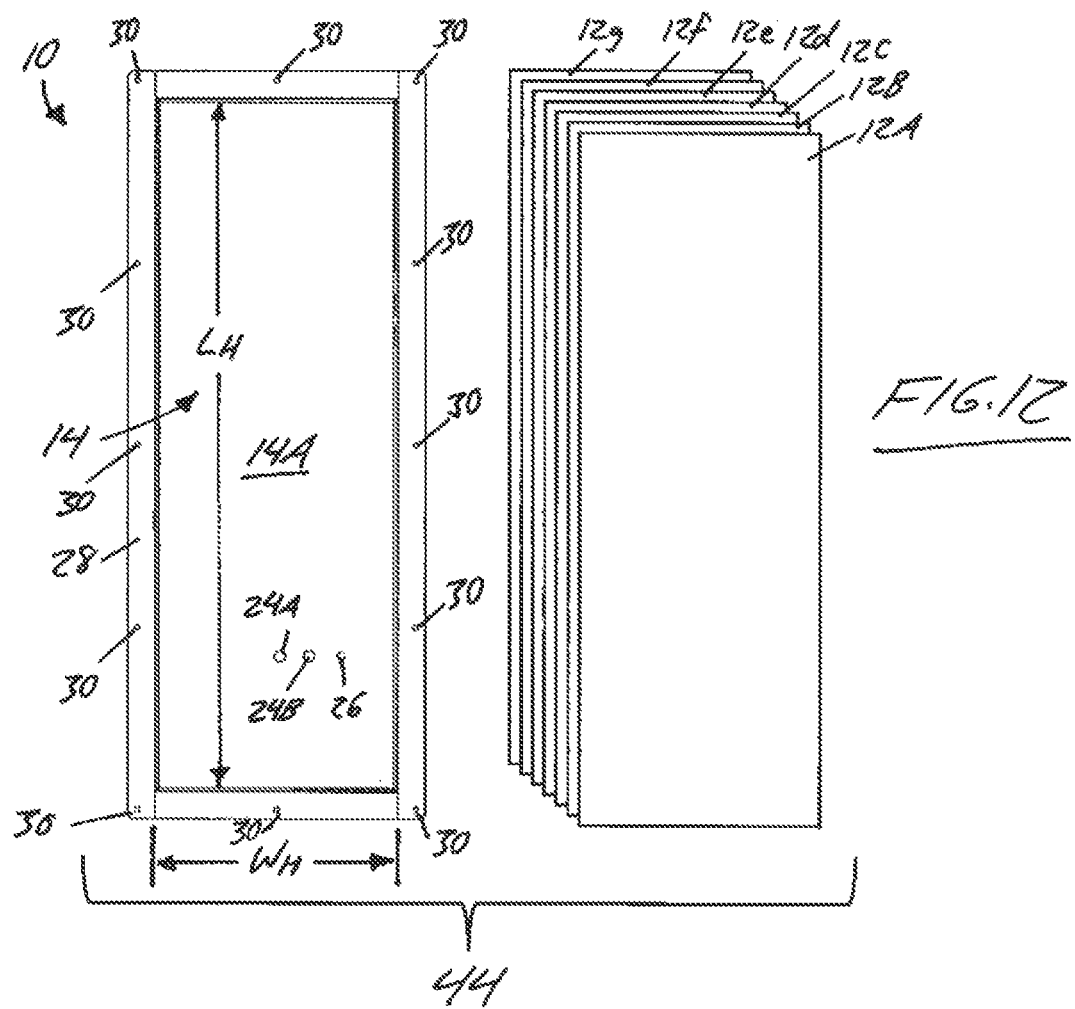
FIG. 12 schematically illustrates provision of the apparatus of FIG. 1 in the form of a kit composed of the air sanitization unit of FIGS. 6 through 9 and an accompanying set of reflectors of the type shown in FIGS. 10 and 11.

In the preferred embodiment shown in the figures, a length $L_R$ of the reflector 12A is roughly equal to a housing length $L_H$ of the air sanitization unit 10, which excludes the mounting flange 28 and is measured between the widthwise perimeter walls 14E, 14F of the housing 14. Likewise, a width $W_R$ of the reflector 12A is preferably equal to a housing width $W_H$ of the air sanitization unit 10, which again excludes the mounting flange, and is measured between lengthwise perimeter walls 14C, 14D of the housing 14. Referring to FIG. 8A, a maximum protruding distance DB reached by the bulb 16 from the rear facial wall 14B of housing is less than the housing length $L_H$, and also less than the housing width $W_H$. FIG. 12 illustrates a preferred implementation of the invention in the form of a kit 44 composed of an air sanitization unit 10 accompanied by a plurality of identical reflectors 12A-12G. Since each reflector 12A-12G is dimensioned roughly equal to the front and rear facial walls 14A, 14B of the housing 14 of the air sanitization unit 10, any one of the identical reflectors 12A-12G can be used as a tracing template to mark off a suitable rectangular cut-out area on the duct wall 108A, which is then cut-out from the duct wall 108A to accommodate mounting of the air sanitization unit 10 in the cut-out opening. FIG. 5A shows a rectangular opening 110 having been cut out from the duct wall 108A in such fashion so that its size roughly matches the rear facial wall 14B of the sanitizer unit's housing 14. By roughly matching, it is meant that the opening 110 is at least as large as the housing's rectangular shape, and typically slightly larger if cut accurately to the traced outline of the equally dimensioned reflector. FIG. 5A shows an array of fastening points 112 distributed around the cut-out opening 110 at matching intervals to the fastening apertures 30 in the flange 28 of the air sanitization unit 10, though these fastening points 112 need not be marked and pre-drilled if self-drilling screw fasteners are used to install the unit 10.

Before inserting the rear working side of the unit 10 into the opening 110 and fastening the mounting flange 28 of the housing 10 in place, the set of reflectors 12A-12G are first inserted into the interior space of the duct 106 through the cut-out opening 110, and are magnetically secured on the interior wall surfaces the second, third and fourth duct walls 108B, 108C, 108D at elevations thereon matching the opening 110 into which the air sanitization unit 10 will then be mounted. The illustrated example represents a scenario in which the reflectors 12A-12G and the rear facial wall 14B of the housing all measure 8-inches by 23-inches, the rectangular duct 106 measures 10-inches by 24-inches (a common duct size), and the overall flanged width of the air sanitization unit measures no more than 10-inches, and preferably slightly less than 10-inches (e.g. between 9.0 and 9.9 inches). This way, the rough 8-inch opening 110 cut centrally in the 10-inch-wide duct wall 108A leaves a 1-inch margin on each side of the opening 110 to accommodate the mounting flange 28 of the unit 10, which is fastened to these intact margins of the duct wall on either side of the opening 110, and preferably also above and below the opening. Meanwhile, placement of a singular reflector 12A in a length-up orientation on the interior surface of the second duct wall 108B in aligned relation across from the opening 110 in the first duct wall 108A means that a substantial majority of the second duct wall's 10-inch width will be covered by the reflector's 8-inch wide reflective surface 38, and owing to the reflector's equal length to that of the housing 14, this reflective surface will also cover an entirety of the elevational range within which the entire bulb 18 of the air sanitizations unit 10 will reside, once the unit 10 is installed.

In addition to the first reflector 12A placed on the second duct wall 108B across from where the air sanitization unit will be mounted, at least one additional reflector is also magnetically mounted on the interior surface of each of the duct's remaining wider third and fourth walls 108C, 10D, once again at this same elevational range corresponding to the cut-out opening 110 in the first duct wall 108A. In the illustrated example, where the duct 106 is 24-inches wide and the reflectors are each 23-inches long, three reflectors 12B, 12C, 12D are shown mounted on the third duct wall 10C in stacked relation one over the other, each in a width-up orientation placing the reflector's length in crosswise width-spanning relationship to the third duct wall 108C. Another three reflectors 12E, 12F, 12G are likewise mounted to the fourth duct wall 108D in this same stacked, width-up orientation of width-spanning relationship to the duct wall 108D. The respective 8-inch widths of the three reflectors on each wide wall 108C, 108D of the duct thus collectively span an entirety of the full 23-inch elevational span of the opening 110 in the first duct wall 108A, while the 23-inch length of each such reflector 12B-12G spans a substantial majority (23⁄24ths) of the duct wall on which it is mounted. Accordingly, a substantial entirety of interior wall surfaces of the second, third and fourth duct walls 108B-108D, within the elevational span of the opening 110 in which the unit 10 will now be mounted, are lined by the magnetically installed reflectors 12A-12G, whose reflective surfaces 38 face inwardly from the duct walls on which they are mounted. The multiple reflectors on the wide duct walls 108C, 108C may alternatively be placed side by side to one another in length-up orientations to accomplish the same effective full-width, full-elevation coverage, given suitable relative dimensions of the reflectors and duct walls.

The rear working side of the air sanitization unit 10 is then inserted into the opening 110 in the first duct wall 108A, and the mounting flange 28 of the housing 14 is fastened in place to the exterior of the first duct wall 108A on all four sides of the opening 110 therein. The UV emitter 16 is thereby placed into the duct's interior space, in a position residing close to, but offset a short distance inward from, the first duct wall 108A. Since the bulb axes 22A-22D are all parallel to the rear facial wall 14B of the housing 14, and likewise parallel to the first duct wall 108A to which the housing is now mounted, the bulb 18 is of little protrusive relation to overall cross-sectional flow area of the duct, spanning only a minor fraction of the duct's interior width. Nonetheless, effective UV coverage of the duct's cross-sectional flow area is achieved by reflection of incident UV light from the bulb 18 off the installed reflectors that substantially cover the interior wall surfaces, as schematically illustrated by reflected light rays in FIG. 4.

While the illustrated example in FIGS. 1 and 2 shows multiple reflectors being installed in stacked relation one over another on the wide duct walls to collectively cover the entire elevational range of the opening 110 and installed unit 10, or to at least cover the entire elevational range of the bulb(s) 18 of the unit 10, it will be appreciated that this may not be necessary, and the installed quantity of reflectors may be reduced, for example to as few as one reflector per duct wall, even at the wider walls of the duct, while still accomplishing a thorough sheet of incident and reflected light spanning an effective entirety of the duct's cross-sectional flow area. It will also be appreciated that while the illustrated embodiment employs a plurality of identically sized reflectors, differently sized reflectors in various combinations and quantities may alternatively be employed. For example, reflectors in a variety of dimensions chosen to match common duct sizes may be provisioned, and supplied to customers in user-specific kits specifically sized for their intended application.

It will also be appreciated that the invention is not limited to installation specifically on a return air duct, and for example may alternatively be used on a supply air duct, nor is the invention limited to use on an upright duct, use in a residential HVAC system, or use on a duct whose dimensions are such that a substantially full width of the supporting duct wall of the unit 10 is spanned by the installed unit. In instances where the unit 10 spans notably less than the width of the duct wall on it is installed, one or more additional reflectors may optionally be placed on the same wall as the unit 10, in positions situated beside the opening 110 in that same duct wall. While the magnetic securement of the reflectors is ideal in terms of convenient tool-free installation thereof in a manner that maintains the integrity of the duct walls on which they are installed, it will be appreciated that other means of securing the reflectors in place may alternatively be employed.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. An in-duct air sanitization apparatus comprising:
   an air sanitizer comprising:
   a housing configured for mounting thereof in an opening cut in a wall of an HVAC duct inside of which a forced airflow is to be sanitized, said housing containing therein electronic operating components of said air sanitizer; and
   a UV emitter supported on said housing in a position residing outside the housing at a rear working side thereof that faces into the HVAC duct when said housing is installed in the opening cut in said wall of the HVAC duct, said UV emitter being operable by said electronic operating components to irradiate an interior of said HVAC duct with UV light, and said UV emitter comprising one or more UV bulbs composed of one or more tubular segments that each have a longitudinal axis along which the tubular segment is elongated, and that each lies in an orientation that is generally parallel to said working side of housing such that said one or more tubular segments lie generally parallel to said wall of the HVAC duct;
   wherein said housing comprises:
   a front side of opposing relationship to said rear working side;
   perimeter walls projecting from the rear working side of housing toward the front side at perimeter boundaries of said rear working side;
   an interior space that is delimited between of said front side of the housing, said rear working side of the housing and said perimeter walls of the housing, which interior space contains said electronic operating components; and
   mounting features residing at locations outwardly from said perimeter walls and said perimeter boundaries of the rear working side and by which said housing is mountable to said wall of the HVAC duct, at an exterior thereof facing oppositely away from the interior of said HVAC duct, at intact margins of said wall of the HVAC duct that surround said opening cut therein; and
   wherein a furthest distance that is reached from the rear working side of the housing by any of said one or more tubular segments of the one or more UV bulbs is less than a length of said housing, as measured between an opposing pair of the perimeter walls of the housing.

2. The apparatus of claim 1 further comprising one or more reflectors that are defined separately of the housing and are mountable independently thereof on one or more interior wall surfaces of the HVAC duct, at one or more walls thereof other than said wall of the HVAC duct at which said housing is mountable in the opening cut therein, to receive and reflect incident light from the UV emitter at sides of the duct unoccupied by said housing.

3. An in-duct air sanitization apparatus comprising:
   an air sanitizer comprising:
   a housing configured for mounting thereof in an opening cut in a wall of an HVAC duct inside of which a forced airflow is to be sanitized, said housing containing therein electronic operating components of said air sanitizer; and
   a UV emitter mounted on a working side of the housing that faces into the HVAC duct when installed thereon and operable to irradiate an interior of said HVAC duct with UV light, said UV emitter comprising one or more UV bulbs composed of one or more tubular segments that each have a longitudinal axis along which the tubular segment is elongated, and that each lie in an orientation that is generally parallel to said working side of housing such that said UV emitter lies generally parallel to said wall of the HVAC duct; and
   one or more reflectors that are defined separately of the housing and are mountable independently thereof on one or more interior wall surfaces of the HVAC duct, at one or more walls thereof other than said wall of the HVAC duct at which said housing is mountable, to receive and reflect incident light from the UV emitter at one or more sides of the duct unoccupied by said housing and said UV emitter
   wherein a furthest distance that is reached from the rear working side of the housing by any of said one or more tubular segments of the one or more UV bulbs is less than a length of said housing, as measured between an opposing pair of the perimeter walls of the housing.

4. The apparatus of claim 3 wherein each reflector the one or more reflectors are each uniplanar so to lay flat against the one or more interior wall surfaces.

5. The apparatus of claim 3 wherein said one or more reflectors comprise a plurality of reflectors mountable to multiple interior wall surfaces of the HVAC duct at multiple sides thereof unoccupied by said housing and said UV emitter.

6. The apparatus of claim 5 wherein said plurality of reflectors include at least three reflectors mountable to the interior wall surfaces of the HVAC duct at three walls thereof.

7. The apparatus of claim 5 in combination with HVAC duct, wherein said plurality of reflectors are of equal width to one another, and each possess a reflector width that is no greater than a half interior width of a wide duct wall of the HVAC duct, and said one or more UV bulbs occupy only a minor fraction of an interior width of the duct measured parallel to said half interior width of said wide duct wall.

8. The apparatus of claim 5 wherein said plurality of reflectors comprise at least four reflectors of equal size to one another, of which at least a pair of said reflectors are installable on a same wide duct wall of the HVAC duct, and a singular reflector is installable on a narrow duct wall of the HVAC duct.

9. The apparatus of claim 3 in combination with said HVAC duct, wherein the air sanitizer is mounted to a first wall of the HVAC duct, and said one or more reflectors are mounted to said one or more interior wall surfaces of said HVAC duct at said one or more sides there unoccupied by the housing and the UV emitter, and said one or more UV bulbs occupy only a minor fraction of an interior width of the duct measured parallel from said first wall of the HVAC duct to a second wall of the HVAC duct that resides oppositely of said first wall.

10. The combination of claim 9 wherein said one or more reflectors comprises a set of multiple reflectors occupying multiple walls of the HVAC duct, including said second wall of the HVAC duct that resides oppositely of the first wall on the which the air sanitizer is mounted, and third and fourth walls of the HVAC duct that resides opposite of one another and span between the first and second walls of the HVAC duct.

11. The combination of claim 10 wherein said first and second walls of the HVAC duct are narrow walls of lesser width than said third and fourth walls, and the multiple reflectors comprise a singular reflector residing on the second wall of the HVAC duct, at least two reflectors residing on the third wall of the HVAC duct, and at least another two reflectors residing on the fourth wall of the HVAC duct.

12. A method of installing an UV-based air sanitizer in an HVAC duct that has a plurality of duct walls delimiting an interior duct space having a cross-sectional flow area, said method comprising:
(a) to an interior wall surface of a subset of said duct walls, mounting one or more reflectors for the purpose of receiving and reflecting incident UV light from the air sanitizer to create thorough UV coverage throughout said cross-sectional flow area of the duct; and
(b) separately and independently of the one or more reflectors mounted to said subset of said duct walls, mounting said UV-based air sanitizer in an opening cut in a first one of said duct walls, other than said subset of the duct walls to which said one or more reflectors is mounted, in an installed position in which a UV emitter of said air sanitizer is operable to irradiate the interior duct space, and the one or more reflectors mounted therein, with UV light, and thereby generate said thorough UV coverage throughout said cross-sectional flow area of the duct using reflection of said UV light from the one or more reflectors mounted at said subset of said duct walls
wherein the UV emitter comprises one or more UV bulbs composed of one or more tubular segments, and each of said one or more UV bulbs occupies only a minor fraction of an interior width of the duct, as measured from said first one of the duct walls, to which the UV-based air sanitizer is mounted, to an opposing second one of the duct walls that is situated oppositely of said first one of the duct walls;
wherein said air sanitizer comprises:
a housing configured for mounting thereof in said opening cut in said wall of an HVAC duct inside of which a forced airflow is to be sanitized, said housing containing therein electronic operating components of said air sanitizer; and
said UV bulbs composed of one or more tubular segments, each have a longitudinal axis along which the tubular segment is elongated, and that each lie in an orientation that is generally parallel to said working side of housing such that said UV emitter lies generally parallel to said wall of the HVAC duct.

13. The method of claim 12 wherein step (a) comprises mounting at least one of said reflectors to a wall of the HVAC duct that resides in opposing relation to the wall on which the air sanitizer is mounted in step (b).

14. The method of claim 13 wherein step (a) comprises mounting at least another two of the reflectors to third and fourth walls of the HVAC duct that reside oppositely of one another, and to neither of which the air sanitizer is mounted in step (b).

15. The method of claim 12 wherein step (a) comprises mounting multiple reflectors on at least one of the walls of the HVAC duct.

16. The method of claim 12 wherein the walls of the duct include two narrow walls and two wide walls of greater width than said two narrow walls, and step (a) comprises mounting multiple reflectors to add least one of said two wide walls.

17. The method of claim 16 wherein the first one of the duct walls on which the air sanitizer is mounted in step (b) is one of said two narrow walls, and step (a) comprises mounting multiple reflectors to each of said two wide walls.

18. The method of claim 16 wherein the greater width of the wide walls is at least twice a smaller width of the narrow walls, the reflectors are all of equal width to one another, and step (a) comprises mounting at least two reflectors on said at least one of said two wide walls, and mounting a singular reflector on at least one of the said two narrow walls.

19. The method of claim 18 wherein the first one of the duct walls on which the air sanitizer is mounted in step (b) is one of said two narrow walls, and step (a) comprises mounting at least a respective pair of reflectors on each of said two wide walls, and mounting a singular reflector on the other one of said two narrow walls.

20. The apparatus of claim 1 wherein said furthest distance reached by said any of said one or more tubular segments of the one or more UV bulbs is also less than width of said housing, as measured perpendicularly of the length thereof and between another opposing pair of the perimeter walls.

21. The apparatus of claim 1 further comprising a set of externally projecting standoffs on the working side of the housing by which the one or more UV bulbs are held in externally offset relation from the working side of the housing so as to reside in inwardly offset relation to the wall of the HVAC duct when the housing is mounted thereto.

* * * * *